United States Patent [19]
Ryan

[11] Patent Number: 4,729,959
[45] Date of Patent: Mar. 8, 1988

[54] GLUCOSE REFERENCE CONTROL FOR GLUCOSE TEST STRIPS

[75] Inventor: Wayne L. Ryan, Omaha, Nebr.

[73] Assignee: Streck Laboratories, Inc., Omaha, Nebr.

[21] Appl. No.: 832,068

[22] Filed: Feb. 24, 1986

[51] Int. Cl.$^4$ .......................................... G01N 31/00
[52] U.S. Cl. ...................................... 436/14; 435/14; 436/10; 436/17; 436/18
[58] Field of Search ...................... 436/11-18; 435/14

[56] References Cited

U.S. PATENT DOCUMENTS 3,920,580 11/1975 Mast ........................................ 436/14
4,199,471 4/1980 Louderback et al. ................ 436/17
4,264,470 4/1981 Chastain et al. ......................... 436/8
4,298,498 11/1981 Rehner et al. ......................... 436/14
4,324,686 4/1982 Mundschenk ........................ 252/408

Primary Examiner—Deborah L. Kyle
Assistant Examiner—T. J. Wallen
Attorney, Agent, or Firm—Larson and Taylor

[57] ABSTRACT

A stable glucose reference control has been found in which the true value and the measured value of glucose in blood, colorimetrically obtained with glucose test strips, is approximately the same. The glucose reference control comprises an aqueous suspension of:

(i) 40 to 500 mg/dL of glucose, and
(ii) about 0.1 to $0.3 \times 10^{12}$/dL red blood cells fixed with a fixing agent to render the red blood cells incapable of metabolizing glucose.

12 Claims, No Drawings

GLUCOSE REFERENCE CONTROL FOR GLUCOSE TEST STRIPS

FIELD OF THE INVENTION

This invention relates to a glucose reference control for glucose test strips. More particularly, the present invention is directed to a stable glucose reference control suitable for use in enzymatic test systems that give quantitative measures of glucose.

BACKGROUND OF THE INVENTION

The monitoring of the level of glucose in blood is important to the management of diabetes. The level of glucose in the blood is controlled by the amount of carbohydrate ingested and by insulin. Too much insulin lowers the glucose level and too little will result in an abnormally high level of glucose. Both circumstances lead to serious health problems for the diabetic.

Most of the glucose testing done outside of the hospital laboratory is done in non-laboratory settings such as nurses' stations, physician's offices and at home. Testing is frequently done by measuring the amount of glucose in urine. As the level of glucose rises in the blood it exceeds the ability of the kidney to reasorb and glucose is excreted into the urine.

Although measurement of glucose in urine is useful, measurement of glucose in blood provides a more accurate reflection of the condition of the subject. Urine glucose does not accurately reflect the level of glucose in the blood since the level of glucose in urine is determined by the level of glucose in the blood and the ability of the kidney to reabsorb the glucose. Therefore, the urine sample cannot tell the diabetic how low his glucose level is.

Dry reagent test strips are widely used for detecting glucose in urine and blood. In general, such test strips comprise plastic strips provided at one end thereof with an absorbent paper portion impregnated with an enzyme system and a color indicator compound which changes color when oxidized. The change in color can be measured by comparing the color formed on the strip with a standard color chart calibrated to various glucose concentrations. More recently, however, to more accurately control the level of glucose in blood, instruments have been developed to measure the color change in a reflectance photometer and thereby give quantitative results.

Although aqueous glucose control samples are provided with these test systems, it is recognized that the controls are not adequate. This is because the values of the aqueous controls do not correspond to the actual glucose control due to factors, principally red blood cells, which are absent in the aqueous controls.

This problem is best seen by making a solution of glucose in water and determining the true value of glucose vs. the value obtained with commercially available glucose test strips. For example:

|  | True Value | | Measured Value |
|---|---|---|---|
| Chemstrip bG ® (1) | 80 mg/dL | = | 115 mg/dL |
| Dextrostix ® (2) | 80 mg/Dl | = | 149 mg/dL |

(1) A trademark of Bio-Dynamic/Boehringer Mannheim Diagnostics, Inc.
(2) A trademark of Ames Division of Miles Lab.

Thus, a definite need exists for a stable quality control system for the glucose meter. This need is discussed in two recent articles: von Schenck H, Lonnstrom L and Engstrom M; Quality control of reflectometric determinations of glucose in dried blood spots on filter paper; Clin Chem 31(5):706, 1985; and Burrin JM, Williams DRR and Price CP. Performance of a quality-assessment scheme for blood glucose meters in general practice. Ann Clin Biochem 22:148, 1985. After stressing the poor performance of the strips and the need for a quality control system, both articles suggest the use of filter paper discs containing boric acid to absorb the blood. The blood is then sent to the clinical laboratory for assay. However, the method proposed by the articles has proved ineffective because quality control assessment occurs several days after the test is performed and, therefore, the information is of limited usefulness. The method is also expensive because of the separate assay required.

Similar elevated values obtained with strips are seen for other levels of glucose. The reason for the lack of agreement between the real value and the determined value is not known for certain but it is probably due to the more rapid penetration of the aqueous glucose control solution into the strip as compared to that with blood. In any case, presently available aqueous solutions of glucose are not acceptable controls for the test strips.

A further problem is that the validity of the aqueous glucose control solution cannot be verified by using standard clinical laboratory methods of analysis commonly employed in the hospital (standard methods of analysis give the actual value).

Accordingly, it is the object of the invention to provide a stable glucose reference control with glucose test strips, in which the true value of glucose and the measured value of glucose determined colorimetrically with glucose test strips is approximately the same.

SUMMARY OF THE INVENTION

This and other objects of the invention are obtained by a glucose reference control for glucose test strips comprising an aqueous suspension of
(i) about 40 to 500 mg/dL of glucose, and
(ii) about 0.1 to $0.3 \times 10^{12}$/dL of red blood fixed with a fixing agent to render said red blood cells incapable of metabolizing glucose. Preferably, the aqueous suspensions of the invention comprise about 60 to 300 mg glucose per dL and about 0.2 to $0.3 \times 10^{12}$/dL of red blood cells.

During the course of the development of the present invention, attempts were made to formulate glucose reference controls by adding glucose to suspensions of red blood cells since it was believed that the reason aqueous control solutions did not give the actual values for glucose was the absence of red blood cells. The result was a rapid disappearance of glucose due to the tendency of the red cells to metabolize the glucose. Attempts to block the metabolism were unsuccessful until the red blood cells were "fixed" by treatment with red blood cell fixing agents. The resulting fixed red blood cells were surprisingly found to be incapable of metabolizing the added glucose presumably because the fixing treatment inhibited enzymes present in the red blood cells.

In a preferred aspect of the invention, the reference control includes an alkali metal borate, an alkali metal phosphate or mixtures thereof. It has been unexpectedly discovered that the presence of these salts in the glucose reference control solution further assists in bringing the measured value closer to the actual value. The preferred phosphates are the meta-, pyro- and ortho phosphates of sodium and potassium and the preferred alkali metal borate is sodium borate. When employed, the salts are added in about 0.2 to 0.5 molar, preferably about 0.1 molar concentration.

Fixed red blood cells according to the present invention can be obtained by using conventional red blood cell fixing agents known in the art as, for example, aldehydes, such as formaldehyde and glutaraldehyde, tannic acid, an imidinating agent such as dimethylsuberimidate or other chemical fixative agents. Any animal red blood cells can be utilized but human and bovine red blood cells are preferred.

Fixing of the red blood cells is readily accomplished by treating a suspension of the red blood cells with a sufficient concentration of the fixing agent. The amount of fixing agent added to the suspension of red blood cells will vary depending upon the number of cells in suspension being treated and the fixing agent employed. In the case of aldehyde and imidinating fixing agents, the concentration will usually vary from 0.004 to 0.10% by weight per $0.1 \times 10^{12}$/dL of red blood cells. In all cases, the reaction of the fixing agent with the red blood cells is allowed to proceed until their ability to metabolize glucose is completely inhibited. The fixing period necessary to achieve this result ordinarily takes about 24 to 48 hours.

The level of glucose is chosen to reflect normal, hypoglycemia or hyperglycemia blood levels.

The optimum number of fixed red blood cells employed in any given glucose reference control of the invention will vary depending upon several factors. To obtain a good agreement between true value and measured value, more red cells are required at the low levels of glucose. However, this same higher concentration of red cells can be used for both the lower and higher concentrations of glucose.

The testing systems with which the glucose reference control of the invention can be used are any of those which measure glucose in blood by use of dry reagent glucose test strips. Such test strips utilize an enzymatic system wherein the glucose content is determined colorimetrically, visually or by reading the color change with a reflectance photometer. Illustrative of these test systems are glucose test strips which use either glucose oxidase, hexokinase or glucose dehydrogenase, all briefly discussed below under separate headings.

GLUCOSE OXIDASE/PERIOXIDASE METHOD

Glucose oxidase ($\beta$-D-glucose: oxygen 1-oxidoreductase EC 1.1.3.4) from *Aspergillus niger* oxidizes glucose according to the following reaction:

D-glucose + $O_2$ → D-gluconic acid + $H_2O_2$.

The $H_2O_2$ found in the oxidase reaction may be measured colorimetrically through the use of a coupled enzyme in which the $H_2O_2$ formed is coupled via peroxidase to a chromogenic $O_2$ acceptor which undergoes a color change. Examples of suitable $O_2$ acceptors are O-dianisidine, O-tolidine, 3-methyl-1-benzothiazolinone hydrazone (MBTH), 2,2'-azino-di-(3-ethyl-benzthiazoline)-6- sulphonate (ABTS) and 4-aminophenazone and other benzidine type indicators such as are described in U.S. Pat. No. 4,340,392, hereby incorporated by reference.

HEXOKINASE/GLUCOSE-6-PHOSPHATE DEHYDROGENASE

Glucose may be determined using hexokinase (ATP: D-hexose-6-phosphotransferase EC 2.7.1.1.) and glucose-6-phosphate dehydrogenase (D-glucose-6-phosphate: NADP oxidoreductase EC 1.1.1.49) according to the following reactions:

$$\text{D-Glucose} + \text{ATP} \xrightarrow[\text{Mg}^{++}]{\text{HK}} \text{Glucose-6-PO}_4 + \text{ADP}$$

$$\text{Glucose-6-PO}_4 + \text{NADP}^+ \xrightarrow{\text{G-6-PDH}}$$

$$\text{6-phosphogluconate} + \text{NADPH} + \text{H}^+$$

The NADPH generated in the second step is proportional to the glucose present and may be measured by absorbance at 340 nm or by fluorescence at 456 nm.

GLUCOSE DEHYDROGENASE/NAD

Glucose dehydrogenase (B-D-glucose: NAD oxidoreductase, EC5.1.3.3) from *B. megaterium* or *B. cerus* provides another enzymatic method for determining glucose. The enzyme is NAD dependent and offers the following single step method for measuring glucose:

$$\text{D-glucose} + \text{NAD} \xrightarrow{\text{glucose dehydrogenese}}$$

$$\text{D-gluconolactone} + \text{NADH} + \text{H}^+$$

The NADH produced can be measured directly at 340 nm.

Examples of commercially available testing systems, i.e. instruments and strips that may be used are as follows:

| Instrument | Strip | Manufacturer |
| --- | --- | --- |
| 1. Accu-Check bG ™ Blood Glucose Monitor | Chemstrip bG ® | Bio-Dynamics/Boehringer Mannheim Diagnostics, Inc. Indianapolis, IN |
| 2. Glucoscan ™ | Glucoscan Test Strips | Lifescan, Inc. Mountain View, CA |
| 3. Glucometer ® Reflectance Photometer | Dextrostix ® Reagent Strips | Ames Division, Miles Lab. Elkhart, IN |
| 4. Beta Scan Trendsmeter ™ | Trendstrip ™ | Orange Medical Instruments Costa Mesa, CA |
| 5. Ames Glucometer ® Reflectanct Photometer | BetaScan Reagent Strips | Orange Medical Instruments Costa Mesa, CA. |

The suspension medium containing the fixed human blood cells and glucose is one non-deleterious to said cells. The suspension medium can be water alone but is preferably a physiological solution buffered to a pH neutral to alkaline, preferably a pH of 7 to 9. The preferred buffering agents are the alkali metal phosphates and borates mentioned above.

If desired, any of the adjuvants commonly added to glucose reference controls such as common salts, preservatives, and the like can be included in the glucose reference control of the invention.

Examples of preservatives that may be used include potassium sorbate, nalidixic acid, amikacin, gentamicin and combinations thereof. The preservative may be included in an amount corresponding to accepted levels e.g. about 0.01% to 0.3%.

Suitable common salts, other than the preferred phosphate and borate salts described above, include alkali metal halides, sulfates and bicarbonates such as sodium chloride, potassium chloride, sodium sulfate, potassium sulfate, sodium bicarbonate, potassium bicarbonate and the like. Satisfactory reference controls are obtainable with 0 to 15% salt solution. When used, the salt solution is preferably a 0.1 to 0.5 M solution.

Any convenient method can be used to formulate the glucose reference control of the invention. One preferred procedure involves first making up an aqueous glucose solution by adding to distilled water glucose and optionally, the phosphate or borate salt of the preferred embodiment of the invention and any other adjuvants desired. An acid such as HCl is then added bringing the pH of the solution to approximately 7.3. The resulting solution is filtered and the fixed red blood cells are suspended therein. The suspension is centrifuged and storage diluent removed. The suspension is washed by adding thereto more glucose diluent, resuspending the cells and again removing storage diluent.

The wash cycle is repeated and after the last wash, fresh glucose diluent is added in an amount that brings the level of red blood cells to 15-20 volume % or a hematocrit of 17-20.

EXAMPLE I

Preparation of Fixed Human Red Blood Cells

Human red blood was collected in a citrate anticoagulant and the blood is centrifuged to remove the plasma. The red blood cells were counted and the concentration of cells adjusted to $1 \times 10^6/mm^3$ by addition of phosphate buffered saline having a pH of 7.4. Glutaraldehyde or Dimethylsuberimidate were then slowly added to the red cells with mixing until a final concentration of 0.12% fixing agent was provided. The reaction was allowed to proceed overnight at 6° C. and the cells centrifuged and washed with phosphate buffered saline.

EXAMPLE II

Preparation of Reference Control of Invention

To approximately 900 mL distilled water were added 9.5 gm/L PO$_4$ anhydrous dibasic sodium phosphate, 60 mg % glucose (dextrose), 100 mg/100 ml potassium sorbate, 2.5 mg/100 mL Nalidixic acid, 1.0 mg/100 mL Amikacin and 2.5 mg/100 mL Gentamicin. Sufficient 1.0 M HCl was introduced to bring the pH to 7.5 and more water added to bring the volume to 1000 mL. The mixture was filtered by gravity through 0.2 μm pore sterile filter.

Two more 1000 mL formulations were prepared by the identical procedure except that the glucose level was 160 mg/dl and 250 mg/dl. To each of the diluents is added the fixed red cells so that the red cell concentration is $1-3.0 \times 10^6/mm^3$ and a hematocrit of 17-20. This is done by centrifuging the suspended red cells to remove the storage diluent. The cells are resuspended in each of the glucose diluents. The wash cycle is repeated to provide complete exchange of diluent and the red cell concentration finally adjusted to 15-20%. The glucose levels are then assayed by standard assay methods such as the YSI glucose analyzer (Yellow Springs Instrument Co. Inc., Yellow Springs, Ohio).

EXAMPLE III

Effect of Salts in Reference Control

To glucose reference controls prepared as described in Examples I and II above and containing 80 or 160 mg/dL of glucose were added the sodium salts identified in Table 1 in the molarities indicated. Accu-Chek ® readings were taken and the results of the tests are reported in Table 1.

TABLE 1

| Salt Molarity | Salt Solutions on Accu-Chek ® Strip Response to 80 and 165 mg/dL of Glucose | | | | |
|---|---|---|---|---|---|
| | Sodium Phosphate | Sodium Citrate | Sodium Acetate | Sodium Chloride | Sodium Borate |
| | Accu-Chek ® Reading at 80 mg/dL | | | | |
| 0.11 | 89 | 104 | 117 | 110 | 88 |
| 0.18 | 87 | 100 | 105 | 112 | 75 |
| 0.25 | 84 | 87 | 102 | 114 | 53 |
| 0.40 | 84 | 94 | 99 | 116 | 52 |
| | Accu-Chek ® Reading at 165 mg/dL | | | | |
| .08 | 180 | 190 | 190 | 195 | 161 |
| .11 | 171 | 172 | 180 | 192 | 151 |
| .18 | 162 | 170 | 173 | 182 | 90 |
| .25 | 161 | 159 | 176 | 178 | 87 |

The data of Table 1 shows that the optimum level of salt required to bring the measured and actual values together depends on the level of glucose. Of the salts tested only sodium borate and sodium phosphate proved effective in bringing the measured glucose value closer to the actual value.

EXAMPLE IV

Different phosphates were added to glucose reference controls prepared as described in Examples I and II above and containing 80 mg/dL or 165 mg/dL glucose. Accu-Chek ® readings were taken and the results are reported in Table 2 below.

TABLE 2

| Salt Molarity | Comparison of Different Phosphates | | | |
|---|---|---|---|---|
| | Sodium Phosphate[1] Meta | Sodium Phosphate[2] Pyro | Sodium Phosphate[3] Ortho | Potassium Phosphate[4] |
| | Accu-Chek ® Reading 80 mg/dL Glucose | | | |
| .05 | 97 | 93 | 90 | 95 |
| .10 | 88 | 89 | 86 | 91 |
| .20 | 90 | 90 | 84 | 93 |
| .30 | 87 | 85 | 81 | 88 |
| | Accu-Chek ® 165 mg/dL Glucose | | | |
| .05 | 165 | 179 | 167 | 181 |
| .10 | 156 | 171 | 164 | 172 |
| .20 | 142 | 146 | 153 | 175 |
| .30 | 140 | 145 | 145 | 165 |

The data of Table 2 shows that all the phosphates tested produced about the same results with potassium phosphate slightly less effective.

EXAMPLE V

A glucose reference control was prepared using the general procedure described in Example II and contained human red blood cells fixed with glutaraldehyde suspended in phosphate buffer (15 g/L pH 7.4) and 150 mg/dL glucose. Potassium sorbate (1.0 g/Liter) and gentamycin (0.2 g/Liter) were added to the reference control as preservatives. For purposes of comparison an identical reference control was prepared but with unfixed red blood cells. The glucose level of each control was checked periodically over a 17 day period. The results are reported in Table 3.

TABLE 3

Stability at 25° Glucose Control in RBC

| Day | Fixed RBC mg/dL | Day | Non-Fixed RBC mg/dL |
|---|---|---|---|
| 1 | 149 | 1 | 140 |
| 4 | 155 | 4 | 110 |
| 7 | 148 | 7 | 60 |
| 10 | 149 | 10 | 65 |
| 13 | 151 | 13 | 58 |
| 17 | 148 | 17 | — |

The data shows that the glucose level of the control containing the fixed red blood cells remained unchanged for 17 days at 25° C., indicating complete inhibition of the enzymes. In contrast, the glucose level of the control containing unfixed red blood cells decreased rapidly.

It is claimed:

1. A glucose reference control for glucose test strips consisting essentially of an aqueous suspension of:

(i) about 40 to 500 mg/dL of glucose, and
   (ii) about 0.1 to $0.3 \times 10^{12}$/dL red blood cells fixed with a fixing agent to render said red blood cells incapable of metabolizing glucose, the number of said fixed red blood cells being sufficient to provide a glucose reference control for glucose test strips in which the true value of glucose and the measured value is approximately the same.

2. A glucose reference control according to claim 1 wherein the fixing agent is an aldehyde.

3. glucose reference control according to claim 2 wherein the aldehyde is glutaraldehyde.

4. A glucose reference control according to claim 1 wherein the fixing agent is an imidinating agent.

5. A glucose reference control according to claim 4 wherein the imidinating agent is dimethylsuberimidate.

6. A glucose reference control according to claim 1 including a phosphate buffer.

7. A glucose reference control according to claim 6 wherein the phosphate buffer is sodium phosphate.

8. A glucose reference control according to claim 1 wherein the fixed human red blood cell concentration is about 0.2 to $0.3 \times 10^{12}$/dL.

9. A glucose reference control according to claim 1 wherein the fixed red blood cell concentration is $0.3 \times 0.10^{12}$/dL.

10. A glucose reference control according to claim 1 wherein the glucose content is about 60 mg to 250 mg/dl.

11. A glucose reference control according to claim 1 wherein the red blood cells are human red blood cells.

12. A glucose reference control according to claim 1 wherein the red blood cells are bovine red blood cells.

* * * * *